United States Patent [19]

Hoelderich et al.

[11] Patent Number: 4,711,930
[45] Date of Patent: Dec. 8, 1987

[54] HONEYCOMB CATALYST AND ITS PREPARATION

[75] Inventors: Wolfgang Hoelderich; Werner Biffar, both of Frankenthal; Matthias Irgang, Heidelberg; Wolf D. Mross, Frankenthal; Michael Kroener, Mannheim; Eberhard Ambach, Limburgerhof, all of Fed. Rep. of Germany

[73] Assignee: BASF Aktiengesellschaft, Ludwigshafen, Fed. Rep. of Germany

[21] Appl. No.: 875,572

[22] Filed: Jun. 18, 1986

[51] Int. Cl.$^4$ .................. B01J 23/84; B01J 27/18
[52] U.S. Cl. ................... 502/209; 502/210; 502/211; 502/213; 502/304; 502/312; 502/527
[58] Field of Search ............ 502/312, 527, 209, 210, 502/213, 211, 304

[56] References Cited

U.S. PATENT DOCUMENTS

| | | | |
|---|---|---|---|
| 3,112,184 | 11/1963 | Hollenbach | 25/156 |
| 3,755,204 | 8/1973 | Sergeys | 502/527 X |
| 3,905,743 | 9/1975 | Bagley | 425/464 |
| 4,075,283 | 2/1978 | Shiraishi et al. | 502/312 X |
| 4,138,368 | 2/1979 | Kiyomiya et al. | 502/312 |
| 4,253,992 | 3/1981 | Soejima et al. | 502/527 X |
| 4,277,376 | 7/1981 | Paolasini | 502/527 X |

FOREIGN PATENT DOCUMENTS

| | | | |
|---|---|---|---|
| 3991 | 4/1973 | Japan | 502/312 |
| 9094 | 7/1974 | Japan | 502/312 |
| 45691 | 10/1974 | Japan | 502/312 |

*Primary Examiner*—Patrick P. Garvin
*Attorney, Agent, or Firm*—Keil & Weinkauf

[57] ABSTRACT

A honeycomb catalyst consisting of from 30 to 95% by weight, calculated as $Fe_2O_3$, of an iron compound and from 0.1 to 60% by weight, calculated as $Al_2O_3$, $CeO_2$ or $Cr_2O_3$, of an aluminum, cerium and/or chromium compound and/or from 1 to 50% by weight of an alkali metal compound, in particular potassium, calculated as $K_2O$, and/or from 0.2 to 20% by weight, calculated as $MeO_3$, of an element of sub-group 6, preferably $MoO_3$ and $WO_3$, and/or from 0.1 to 20% by weight, calculated as $V_2O_5$, of a compound of vanadium and/or from 0.1 to 20% by weight, calculated as $P_2O_5$, of a compound of phosphorus, a process for the preparation of the honeycomb catalyst, and the use of the catalyst for organic reactions.

6 Claims, No Drawings

HONEYCOMB CATALYST AND ITS PREPARATION

Honeycombs have a wide variety of uses, for example as filter material, as packing in washtowers and distillation columns, as heat shields, etc. It is also known that honeycombs can be used as catalysts or catalyst carriers. For example, honeycombs have been used in heterogeneous catalysis, in particular for the detoxification and catalytic combustion of engine exhaust gases and power station waste gases (German Laid-Open Application DOS No. 2,443,262 and German Published Application DAS No. 2,045,488).

Honeycombs are produced, as a rule, using ceramic materials, eg. cordierite and mullite (U.S. Pat. No. 3,112,184 and German Laid-Open Applications DOS No. 2,254,563 and DOS No. 2,152,490). The honeycombs are either coated directly with a catalytically active material or provided with a special layer on which the actual catalytically active material is applied.

The present invention relates to a honeycomb catalyst consisting of from 30 to 95% by weight, calculated as $Fe_2O_3$, of an iron compound and from 0.1 to 60, preferably from 0.1 to 20, % by weight, calculated as $Al_2O_3$, $CeO_2$ or $Cr_2O_3$, of an aluminum, cerium and/or chromium compound and/or from 1 to 50% by weight of an alkali metal compound, in particular potassium, calculated at $K_2O$, and/or from 0.2 to 20% by weight, calculated as $MeO_3$, of an element of sub-group 6, preferably $MoO_3$ and $WO_3$, and/or from 0.1 to 20% by weight, calculated as $V_2O_5$, of a compound of vanadium and/or from 0.1 to 20% by weight, calculated as $P_2O_5$, of a compound of phosphorus, and a process for its preparation and its use.

The novel honeycombs are generally solid catalysts, ie. the material consists entirely of catalytically active material, in contrast to the conventional honeycomb catalysts in which the active component is applied on to a carrier. The honeycomb is difficult to produce and requires a high degree of technical know-how. It was therefore all the more surprising that it was possible to produce the novel honeycombs from a mixture of the starting materials, eg. metal oxides, ie. from a non-ceramic material which, because of its rheological behavior, is usually particularly suitable for extrusion.

The starting mixtures for the preparation of the novel catalysts are composed of a plurality of components:

Component (a) comprises one or more iron compounds which are preferably present in the catalyst in an amount of from 30 to 95% by weight, calculated as $Fe_2O_3$. Various iron oxides and iron oxide hydroxides can be used as iron compounds for the preparation of the catalyst. Examples of suitable compounds are the reddish brown or yellow iron oxide pigment or the black one.

A chromium compound, a cerium compound and/or an aluminum compound are used as component (b), in an amount of from 0.1 to 60, preferably from 0.1 to 20, % by weight, calculated as $Cr_2O_3$, $CeO_2$ or $Al_2O_3$. In the catalyst, these components act to stabilize the structure and prolong the life of the catalyst mixture.

The starting mixture contains, as component (c), from 1 to 50, preferably from 3 to 40, % by weight of an alkali metal compound, in particular a potassium compound, calculated as $K_2O$. The type of potassium compound used depends on the method of preparation. The compounds chosen are preferably those which partially decompose during calcination of the catalyst to give $K_2O$; examples are the hydroxide, the carbonate, the bicarbonate, the carboxylate, the borate and the phosphates of potassium. Preferably, potassium is mixed into the mixture of the remaining catalyst components in the form of potassium hydroxide solution, to promote slurrying during preparation of the honeycomb. Compounds of different alkali metals may also be used together.

A compound of an element of sub-group 6 of the periodic table can be used as component (d). This compound is particularly preferably used in an amount of from 0.2 to 20% by weight, calculated as $MeO_3$; in particular, compounds of the elements molybdenum ($MoO_3$) and tungsten ($WO_3$) are employed. For the preparation of the catalyst, the elements are advantageously used in the form of the oxyacids or their ammonium salts or potassium salts of oxidation state +6, since these compounds readily decompose on calcination. The hetero polyacids of molydenum and tungsten with phosphoric acid, eg. phosphotungstic acid or phosphomolybdic acid, are particularly suitable.

Instead of component (d), or together with it, the novel catalyst can contain from 0.1 to 20% by weight, calculated with $V_2O_5$ or $P_2O_5$, of one or more compounds of vanadium or of phosphorus (component (e)). Particularly suitable compounds of vanadium are the oxides, the ammonium salts and the potassium salts of the highest oxidation state, eg. $V_2O_5$, $NaVO_3$ or $KVO_3$. If both a compound of vanadium and a compound of phosphorus are used, the heteropolyacids of vanadium with phosphoric acid, eg. phosphovanadic acid or its ammonium or potassium salt, is preferably chosen. When the potassium salts of these heteropolyacids are chosen, appropriate reductions for component (b) must be made. If phosphorus is used alone, it is employed in the form of the oxide, the acid or the ammonium or potassium salts or is introduced together with component (d), as a heteropolyacid.

The novel catalyst may also contain other additives, for example elements of sub-group 8, such as Co or Ni, elements of sub-group 1, such as Cu or Ag, elements of sub-group 2, such as Zn or Cd, elements of sub-group 4, such as Ti or Zr, elements of sub-group 7, such as Mn, rare earth metals, such as La, Pr or Nd, actinides, such as Th or U, alkaline earth metals, such as Mg, Ca, Sr or Ba, and elements of main groups 4 and 5, such as Pb and Bi.

The novel catalysts are prepared, as a rule, starting from a mixture of the abovementioned components, which is generally molded, or first kneaded and then molded, with water, with or without the addition of potassium hydroxide solution and with the addition of extrusion assistants, such as starch, methylcellulose, graphite, polyethylene glycols, polyvinyl alcohols, polyvinylpyrrolidones, polyacrylates, stearic acid and its metal salts, naphthalene, ammonia, formic acid, oxalic acid or nitric acid, either with a porosity-improving agent, a lubricant or a peptizing agent. Kneading followed by molding, in particular by extrusion, is preferred. The moldings obtained by extrusion are first dried at from room temperature to 160° C. and then calcined at from 300° to 1,000° C., and it may also be advantageous to carry out stepwise precalcination.

The catalysts according to the invention may have various honeycomb forms. The base surface can be circular, oval or polygonal. The length can be several times the cross-section. A large number of parallel channels pass through the elements, the base surface of the said channels likewise being circular, oval, curved or angular. The free cross-section of the flow area, which should be greater than 40%, plays a critical role with regard to achieving a low pressure loss. The strength of the honeycomb imposes restrictions on the size of the free cross-section.

The external dimensions of the moldings are such that the edge length of the base surface is usually up to 150 mm in the case of rectangular parallelepipeds, and the base of this has about the same diameter as in the case of cylinders. The length of the elements above the base surfaces can be greater than 1,000 mm. The internal width of the inner channels is from 0.5 to 20 mm, and the thickness of the internal separating walls is usually from 0.1 to 5 mm.

Moldings similar to honeycombs may also be used. The channels in these moldings run through the element obliquely with respect to the central axis, instead of parallel to the latter, for example in accordance with the principle of the static mixer, eg. Kerapak ® moldings. These moldings increase mixing of the reaction gases in a transverse direction with respect to the central axis, resulting in greater heat exchange between the reactor wall and the inner space. Moldings of solid catalyst material are similar to the honeycombs.

For catalytic reactions involving large heats of reaction, it is advisable, in order to promote heat exchange, to arrange a plurality of honeycombs with parallel channels in the reactor so that mixing zones or static mixers of ceramic or metallic materials (inert or catalytically active) are located between the individual honeycombs in order to ensure thorough mixing of the reaction gases or deliberately to deflect the gases flowing along the reactor wall into the interior of the reactor, and the gases flowing in the interior toward the outside. The novel catalysts can be used in general in organic chemical reactions, for example in dehydrogenation reactions, dehydrocyanization reactions and alcohol elimination reactions. However, the honeycomb catalysts may also be used for high temperature conversion.

The novel honeycomb catalysts have advantages in, for example, highly selective dehydrogenation reactions.

(a) The advantageous kinetic preconditions (large surface area coupled with short diffusion paths in the pore system), which lead to a substantial increase in activity and selectivity.

(b) The low pressure loss over the catalyst bed, which permits greater volume streams per catalyst volume, as well as reactions under reduced pressure.

(c) The use of honeycombs in modular form permits rapid installation and removal of the catalyst, as well as rapid replacement of parts of the catalyst.

(d) The movements of pellets which occur in a fixed bed are absent, with the result that mechanical abrasion is substantially prevented.

(e) The convenient form of the catalyst facilitates transport, processing or regeneration outside the reactor and final disposal and final storage of the catalyst, particularly when processing by a different method may produce dusts which constitute a health hazard.

The Examples which follow illustrate the novel catalysts and their use.

EXAMPLE 1

Catalyst for the thermal dehydrogenation of ethylbenzene to styrene 10,000 g of $\alpha$-FeOOH, 1,596 g of $K_2CO_3$, 190 g of $Cr_2O_3$, 146 g of $V_2O_5$, 115 g of $WO_3$ and 300 g of starch are mixed, and the mixture is made into a slurry with water. After kneading has been carried out for 3 hours, the plastic material is extruded to give honeycombs. The square base surface of the resulting rectangular parallelepipeds has edges 5 cm long. The length of the rectangular parallelepipeds is 40 cm. The 121 internal channels have a square end face with an edge length of 0.36 mm. The thickness of the inner separating walls is 0.55 mm. The honeycombs are dried for 2 days at temperatures increasing to 150° C. The moldings are then calcined for 5 hours at 500° C. and for 1 hour at 850° C.

The catalyst is tested in an electrically heated model reactor, the tube geometry of the reactor being chosen to match up with the molding.

1 kg/hour of ethylbenzene and 1.5 kg/hour of water are vaporized and passed over the catalyst at 610° C. This corresponds to a space velocity of 1 kg of ethylbenzene per kg of catalyst per hour.

Under the stated conditions, a conversion of 52.9%, based on the ethylbenzene passed in, is achieved after an on-stream time of 100 hours. 94.8% of the ethylbenzene which reacts is converted to styrene.

EXAMPLE 2

Catalyst for the thermal dehydrocyanization of formylalaninenitrile to vinylformamide 3,000 g of $\alpha$-FeOOH (iron yellow), 27.6 g of $V_2O_5$, 78 g of $CrO_3$, 81 g of $WO_3$ and 34.5 g of $Li_2CO_3$ are mixed thoroughly with one another. This mixture is then converted to a slurry with 329 g of KOH, 168 g of potato starch and 28 g of methylcellulose, dissolved in 1 l of $H_2O$, and the slurry is thickened for 1 hour in a kneader. The plastic material is extruded to give honeycombs. The square base surface of the resulting rectangular parallelepiped has an edge length of 5 cm.

The length of the rectangular parallelepiped itself is 12 cm. The 36 internal channels have a square end face possessing an internal edge length of 6 mm. The inner separating walls are 1.5 mm thick. These honeycombs are dried for 3 days at room temperature, for 2 hours at increasing temperatures up to 150° C. and for 4 hours at the latter temperature. Thereafter, the moldings are calcined for 1 hour at 500° C. and for 1 hour at increasing temperatures up to 850° C.

10 such honeycombs are installed in an electrically heated stainless steel tube reactor whose geometry is matched with that of the molding. Each honeycomb is separated from the next honeycomb by a 50 mm long static mixer made of ceramic material, eg. Kerapak$^R$. A thin film evaporator is located upstream of the pyrolysis tube. During the reaction, a reaction temperature of 460° C. and a pressure of 30 mbar are maintained. The space velocity is 0.8 kg of formylalaninenitrile per kg of catalyst per hour. 30 l/h of air are fed in simultaneously. A conversion of 97% and a selectivity of 93% are achieved.

EXAMPLE 3

Catalyst for high temperature conversion 25,200 g of $FeSO_4 \cdot 7 H_2O$ and 473 g of $CrO_3$ are dissolved in water and reacted with concentrated $NH_3$ solution while passing in air. The resulting precipitate is filtered off, washed and converted to a slurry with 44.9 g of $NH_4VO_3$, 250 g of starch and a little water. Kneading is carried out for 3 hours, after which the plastic material is extruded to give honeycombs similarly to Example 1.

The catalyst is tested in an electrically heated model reactor, the tube geometry of the reactor being matched up with the molding. The test conditions are as follows:
Amount of catalyst: 1 l $\hat{=}$ 1 honeycomb
Composition of dry gas:
 60% by volume of $H_2$
 20% by volume of CO
 20% by volume of $N_2$
Throughputs:
 3,000 l (S.T.P.).$h^{-1}$ of hydrogen
 1,000 l (S.T.P.).$h^{-1}$ of carbon monoxide
 1,000 l (S.T.P.).$h^{-1}$ of nitrogen
 3,480 l (S.T.P.).$h^{-1}$ of steam
Space velocity (based on dry gas: 5,000 $h^{-1}$
Pressure: 30 bar.

Gas chromatography shows that the CO conversion is 91% at a reaction temperature of 330° C. after an on-stream time of 1 day.

We claim:

1. A honeycomb catalyst essentially consisting of catalytically active materials, said materials comprising
   (a) 30 to 95% by weight, calculated as $Fe_2O_3$, of an iron compound;
   (b) from 0.1 to 60% by weight, calculated as $Al_2O_3$, $CeO_2$ or $Cr_2O_3$, of an aluminum, cerium or chromium compound or a mixture of 2 or 3 of said compounds; and
   (e) and (f) from 0.1 to 20% by weight, calculated as $V_2O_5$ or $P_2O_5$, of a compound of vanadium or a compound of phosphorus or a mixture of a vanadium and a phosphorus compound.

2. A honeycomb catalyst as defined in claim 1, which further contains
   (c) from 1 to 50% by weight of a potassium compound, calculated as $K_2O$.

3. A honeycomb catalyst as defined in claim 2, which further contains
   (d) from 0.1 to 20% by weight, calculated as $MeO_3$, of a molybdenum compound or a tungsten compound or a mixture of said molybdenum and tungsten compounds.

4. A process for producing honeycomb catalysts that essentially consist of catalytically active materials, which process comprises:
   mixing (a) 30 to 95% by weight, calculated as $Fe_2O_3$, of an iron compound,
   (b) from 0.1 to 60% by weight, calculated as $Al_2O_3$, $CeO_2$ or $Cr_2O_3$ of an aluminum, cerium, or chromium compound or a mixture 2 or 3 of said compounds; and
   (e) and (f) from 0.1 to 20% by weight, calculated as $V_2O_5$ or $P_2O_5$, of a compound of vanadium or a compound of phosphorus or a mixture of a vanadium and a phosphorus or a mixture of a vanadium and a phosphorus compound;
   kneading said mixture with water;
   adding to the mixture at least one extrusion assistant;
   molding the mixture to form the shape of the honeycomb, and thereafter drying and calcining the molding.

5. The process of claim 4, wherein a potassium compound is kneaded with said mixture.

6. A process as defined in claim 4, wherein a mixture of starting materials is kneaded with water, the slurry is applied onto an organic material, molding is carried out to give honeycombs, and the organic components are then burned out.

* * * * *

UNITED STATES PATENT AND TRADEMARK OFFICE
CERTIFICATE OF CORRECTION

PATENT NO. : 4,711,930

DATED : December 8, 1987

INVENTOR(S) : HOELDERICH et al.

It is certified that error appears in the above-identified patent and that said Letters Patent is hereby corrected as shown below:

On the title page insert:

-- [30] Foreign Application
   Priority Data
   June 19, 1985 [DE]
   Fed. Rep. of Germany
   .... 35 21 766.9   --.

Signed and Sealed this

Twenty-sixth Day of April, 1988

Attest:

DONALD J. QUIGG

*Attesting Officer*    *Commissioner of Patents and Trademarks*